United States Patent
Tom et al.

(10) Patent No.: US 7,183,414 B2
(45) Date of Patent: Feb. 27, 2007

(54) PROCESSES FOR THE PREPARATION OF BENZOIMIDAZOLE DERIVATIVES

(75) Inventors: Norma J. Tom, Waterford, CT (US); Michael J. Castaldi, Pawcatuck, CT (US); David B. Ripin, Old Saybrook, CT (US)

(73) Assignee: Pfizer Inc, New York, NY (US)

( * ) Notice: Subject to any disclaimer, the term of this patent is extended or adjusted under 35 U.S.C. 154(b) by 288 days.

(21) Appl. No.: 10/875,030

(22) Filed: Jun. 23, 2004

(65) Prior Publication Data

US 2005/0020625 A1 Jan. 27, 2005

Related U.S. Application Data

(60) Provisional application No. 60/482,176, filed on Jun. 24, 2003.

(51) Int. Cl.
*C07D 215/38* (2006.01)
*C07D 215/46* (2006.01)

(52) U.S. Cl. ........................ 546/162; 546/159
(58) Field of Classification Search ................ 546/159, 546/162
See application file for complete search history.

(56) References Cited

U.S. PATENT DOCUMENTS 7,019,147 B1 * 3/2006 Barth et al. .................. 548/125
7,071,337 B2 * 7/2006 Kath et al. ................... 546/159

FOREIGN PATENT DOCUMENTS

WO   WO 01/40217 A1 * 6/2001

* cited by examiner

*Primary Examiner*—D. Margaret Seaman
(74) *Attorney, Agent, or Firm*—Steve T. Zelson; Christian M. Smolizza

(57) ABSTRACT

The present invention relates to a process for preparing a compound of the formula I or a pharmaceutically acceptable salt, prodrug, hydrate or solvate thereof, wherein $R^1$, $R^2$, $R^3$ and $R^4$ are as defined herein. The compound of formula I is useful in the treatment of abnormal cell growth, such as cancer, in mammals.

40 Claims, No Drawings

PROCESSES FOR THE PREPARATION OF BENZOIMIDAZOLE DERIVATIVES

BACKGROUND OF THE INVENTION

The entire disclosure of parent application Ser. No. 60/482,176 filed Jun. 24, 2003 is fully incorporated herein by reference thereto.

This invention relates to novel processes for preparing benzimidazole derivatives that are useful in the treatment of abnormal cell growth, such as cancer, in mammals. This invention also relates to novel processes for preparing intermediates that may be converted to the aforementioned benzimidazole derivatives. Benzimidazole derivatives, intermediates useful in preparing such benzimidazole derivatives and processes for preparing such benzimidazole derivatives and intermediates have been disclosed in International Patent Publication WO 01/40217, published Jun. 7, 2001, and U.S. Provisional Patent Application Ser. Nos. 60/406,524 and 60/417,047, filed Aug. 28, 2002, and Oct. 28, 2002 respectively.

SUMMARY OF THE INVENTION

The present invention relates to a process for preparing a compound of the formula I

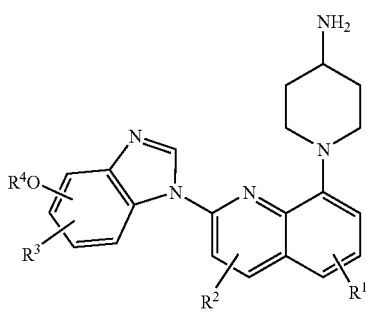

or a pharmaceutically acceptable salt, prodrug, hydrate or solvate thereof; wherein each $R^1$, $R^2$, and $R^3$ is independently selected from the group consisting of H, $(C_1-C_6)$ alkyl, $(C_3-C_6)$cycloalkyl, halo, cyano, $CF_3$, difluoromethoxy, trifluoromethoxy, —$O(C_1-C_6)$alkyl, —$O(C_3-C_6)$cycloalkyl, and —$NR^{12}R^{13}$;

wherein $R^4$ is —$(CR^5R^6)_mH$, or —$(CR^7R^8)_n$(4 to 10 membered)-aromatic or nonaromatic heterocyclic containing one or more heteroatoms each selected from O, S and N, wherein m is an integer ranging from 1 to 5, wherein n is an integer ranging from 0 to 5, wherein said 4 to 10 membered heterocyclic when aromatic is optionally substituted by 1 to 3 $R^9$ substituents, and wherein said 4 to 10 membered heterocyclic when non-aromatic is optionally substituted by 1 to 3 $R^{10}$ substituents at any position and optionally substituted by 1 to 3 $R^{11}$ substituents at any position not adjacent to or directly attached to a heteroatom;

wherein each $R^5$, $R^6$, $R^7$ and $R^8$ is independently selected from the group consisting of H and $(C_1-C_6)$alkyl, such as methyl, ethyl, propyl, butyl and pentyl;

wherein each $R^9$ is independently selected from H, $(C_1-C_6)$alkyl, such as methyl, ethyl, propyl, butyl and pentyl, $(C_3-C_6)$cycloalkyl, halo, cyano, $CF_3$, difluoromethoxy, trifluoromethoxy, —$O(C_1-C_6)$alkyl, —$O(C_3-C_6)$cycloalkyl, and —$NR^{14}R^{15}$;

wherein each $R^{10}$ is independently selected from H, $(C_1-C_6)$alkyl, and $(C_3-C_6)$cycloalkyl;

wherein each $R^{11}$ is independently selected from halo, cyano, $CF_3$, difluoromethoxy, trifluoromethoxy, —$O(C_1-C_6)$alkyl, —$O(C_3-C_6)$cycloalkyl, and —$NR^{16}R^{17}$;

wherein each $R^{12}$, $R^{13}$, $R^{14}$, $R^{15}$, $R^{16}$ and $R^{17}$ is independently selected from the group consisting of H, $(C_1-C_6)$alkyl, and $(C_3-C_6)$cycloalkyl;

wherein each of the aforesaid $(C_1-C_6)$alkyl, $(C_3-C_6)$cycloalkyl, —$O(C_1-C_6)$alkyl and —$O(C_3-C_6)$cycloalkyl substituents wherever they occur may optionally be independently substituted by one to three substituents independently selected from the group consisting of halo, cyano, amino, $(C_1-C_6)$alkylamino, $[(C_1-C_6)$alkyl$]_2$-amino, perhalo $(C_1-C_6)$alkyl, perhalo$(C_1-C_6)$alkoxy, $(C_1-C_6)$alkyl, $(C_2-C_6)$alkenyl, $(C_2-C_6)$alkynyl, hydroxy, and $(C_1-C_6)$alkoxy; comprising reacting a compound of the formula II

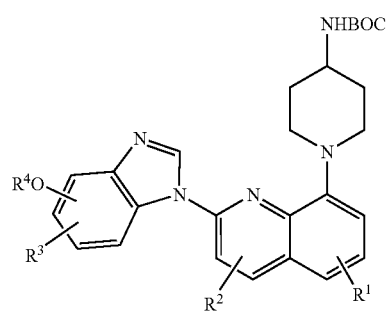

wherein BOC is t-butoxycarbonyl, and $R^1$, $R^2$, $R^3$ and $R^4$ are as defined above for the compound of formula I, with a metal alkoxide, preferably an alkaline earth metal in the presence of water to give a compound of the formula 1. Preferably, the water is present in an amount of about one equivalent (i.e., one equivalent with respect to the compound of formula II). The alkaline earth metal alkoxide is preferably an alkaline earth metal $(C_1-C_6)$alkoxide. The alkaline earth metal is is preferably sodium or potassium, and the $(C_1-C_6)$alkoxide is preferably t-butoxide.

The reaction is preferably conducted in the presence of a solvent, such as an ether. The ether is preferably a cyclic ether, although acyclic ethers may also be used. Examples of suitable ethers include dioxane, dimethoxymethane, diethoxymethane, tetrahydrofuran and 2-methyl tetrahydrofuran, or mixtures of at least two thereof. Tetrahydrofuran, 2-methyltetrahydrofuran or mixtures thereof are especially preferred. Preferably the reaction is conducted at a temperature of about 50° C. to about 110° C., and in a more preferable embodiment at a temperature of about 60° C. to about 80° C.

An embodiment of the present invention refers to thoses processes wherein the 4 to 10 membered heterocyclic is a 4 to 8 membered heterocyclic, in another embodiment a 4 to 6 membered heterocyclic, in another embodiment a 6-membered heterocyclic, in another embodiment a 5-membered heterocyclic and in another embodiment a 4-membered heterocyclic. Another embodiment of the present invention refers to thoses processes wherein m is an integer from 1 to 5, in another embodiment 1, and in another embodiment 2. Another embodiment of the present invention refers to thoses processes wherein n is an integer from 0 to 5, in another embodiment 1, and in another embodiment 2. Another embodiment of the present invention refers to thoses processes wherein when the 4 to 10 membered heterocyclic is aromatic, it may be optionally substituted by 1 R⁹ substituent.

An embodiment of the present invention refers to thoses processes wherein the 4 to 10 membered heterocyclic group is an aromatic heterocyclic group. Examples of suitable of such aromatic heterocyclic groups include: pyridinyl, pyrimidinyl, pyrazinyl, quinolinyl, isoquinolinyl, pyrrolyl, pyrazolyl, imidazolyl, thiophenyl, furanyl, indolyl and benzofuranyl.

Another embodiment of the present invention refers to those processes wherein the 4 to 10 membered heterocyclic group is a non-aromatic heterocyclic group. Examples of suitable non-aromatic heterocyclic groups include tetrahydrothiopyranyl, thiomorpholino, dioxanyl, pyrrolidinyl, tetrahydrofuranyl, tetrahydropyranyl, piperidino, morpholino, piperazinyl, homopiperazinyl, azetidinyl, oxetanyl, homopiperidinyl, 3-azabicyclo[3.1.0]hexanyl, 3-azabicyclo[4.1.0]heptanyl, azabicyclo[2.2.2]hexanyl, 3H-indolyl, and 4H-pyranyl.

Another embodiment of the present invention refers to those processes wherein the 4 to 10 membered aromatic heterocyclic group containing one or more heteroatoms each selected from O, S and N contains one to four heteroatoms each selected from O, S and N, with the proviso that said 4 to 10 membered aromatic heterocylclic does not contain two adjacent O or S atoms. In a preferred embodiment, the 4 to 10 membered hetercyclic group contains one to two O atoms, and in another embodiment one O atom. In another embodiment, the 4 to 10 membered heterocyclic group contains one to two N atoms, and in a preferred embodiment one N atom.

Another embodiment of the present invention refers to those processes wherein the compound of formula I is selected from the group consisting of 1-{2-[5-(3-Morpholin-4-yl-propoxy)-benzoimidazol-1-yl]-quinolin-8-yl}-piperidin-4-ylamine;

(±)-1-{2-[5-(Tetrahydro-furan-3-yloxy)-benzoimidazol-1-yl]-quinolin-8-yl}-piperidin-4-ylamine;

(+)-1-{2-[5-(Tetrahydro-furan-3-yloxy)-benzoimidazol-1-yl]-quinolin-8-yl}-piperidin-4-ylamine;

(−)-1-{2-[5-(Tetrahydro-furan-3-yloxy)-benzoimidazol-1-yl]-quinolin-8-yl}-piperidin-4-ylamine;

1-{2-[5-(3-Methyl-oxetan-3-ylmethoxy)-benzoimidazol-1-yl)-piperidin-4-ylamine;

1-{2-[5-(Tetrahydro-pyran-4-yloxy)-benzoimidazol-1-yl]-quinolin-8-yl}-piperidin-4-ylamine; and the pharmaceutically acceptable salts, prodrugs, hydrates and solvates of the foregoing compounds.

In an especially preferred embodiment, the present invention refers to those processes wherein the compound of formula I is the benezenesulfonate salt of 1-(2-[5-(3-Methyl-oxetan-3-ylmethoxy)-benzoimidazol-1-yl]-quinolin-8-yl}-piperidin4-ylamine.

The present invention also relates to a process for preparing a compound of formula VI

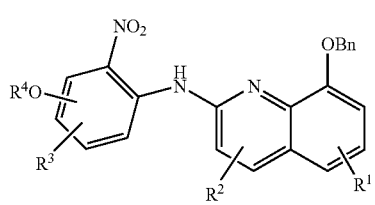

VI wherein Bn is benzyl and wherein R¹, R², R³ and R⁴ are as defined above for formula I; comprising reacting a compound of formula VII

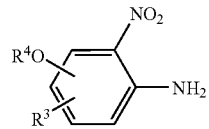

VII wherein R³ and R⁴ are as defined above for formula I, with a compound of formula VIII

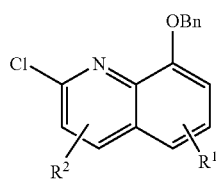

VIII wherein R¹ and R² are as defined above for formula I, in the presence of 1,2-Bis(diphenylphosphino)ethane, a base and a a palladium catalyst, such as a palladium (0) or a palladium (II) catalyst. The palladium catalyst is preferably tris(dibenzylidene acetone) dipalladium (0) or palladium acetate, with the latter being most preferred. Examples of suitable bases include potassium phosphate, sodium t-butoxide and cesium carbonate. One especially preferred embodiment of the present invention refers to those processes wherein the palladium catalyst is palladium acetate, and the base is cesium carbonate. The reaction is preferably carried but in the presence of an aromatic solvent, such as toluene, an ether, such as dioxane, dimethoxyethane, or tetrahydrofuran, or a polar nitrogen-containing solvent such as dimethylformamide (DMF). Solvent mixtures can also be used. The reaction may be carried out at a temperature of of about 90° C. to about 120° C.

An especially preferred embodiment of the present invention refers to those processes wherein R¹ and R² in the compound of formula VII are both hydrogen, and the compound of formula VII is a compound of formula VIIA

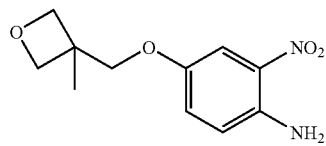

VIIA

The compound of formula VI is useful as an intermediate toward the preparation of the compounds of formula I.

The term "halo", as used herein, unless otherwise indicated, includes fluoro, chloro, bromo or iodo. Preferred halo groups are fluoro and chloro.

The term "alkyl", as used herein, unless otherwise indicated, includes saturated monovalent hydrocarbon radicals having straight or branched moieties. It is understood that for said alkyl group to include cyclic moieties it must contain at least three carbon atoms.

The term "cycloalkyl", as used herein, unless otherwise indicated, includes saturated monovalent hydrocarbon radicals having cyclic (including mono- or multi-cyclic) moieties.

The term "alkenyl", as used herein, unless otherwise indicated, includes alkyl groups, as defined above, having at least one carbon-carbon double bond.

The term "alkynyl", as used herein, unless otherwise indicated, includes alkyl groups, as defined above, having at least one carbon-carbon triple bond.

The term "alkoxy", as used herein, unless otherwise indicated, includes —O-alkyl groups wherein alkyl is as defined above.

The term "solvate", as used herein includes, a compound of the invention or a salt thereof, that further includes a stoichiometric or non-stoichiometric amount of a solvent bound by non-covalent intermolecular forces. Preferred solvents are volatile, non-toxic, and/or acceptable for topical administration to humans.

The term "hydrate", as used herein refers to a compound of the invention or a salt thereof, that further includes a stoichiometric or non-stoichiometric amount of water bound by non-covalent intermolecular forces.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition including 1-oxa-6-aza-spiro[2.5]oct-6-yl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsyate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

In general, "prodrugs" of the compounds of the formula I are functional derivativatives of the compounds of formula I which are readily convertible convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

Compounds referrred to in the processes of the present invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The compounds referred to in the processes of the present invention may have one or more asymmetric centres, and may accordingly exist both as enantiomers and as diastereoisomers. It is to be understood that all such isomers and mixtures thereof are encompassed within the scope of such compounds. Certain compounds of formula I may have asymmetric centers and therefore exist in different enantiomeric forms. All optical isomers and stereoisomers of the compounds of formula I, and mixtures thereof, are considered to be within the scope of the compounds of formula I. The compounds of formula I may include a racemate, one or more enantiomeric forms, one or more diastereomeric forms, or mixtures thereof. The compounds of formula I may also exist as tautomers. Reference to the compound of formula I includes reference to the use of all such tautomers and mixtures thereof.

The term "Me" means methyl, "Et" means ethyl, and "Ac" means acetyl.

The term "DMF", as used herein, unless otherwise indicated, means dimethylformamide.

The term "NMP", as used herein, unless otherwise indicated, means N-methylpyrrolidinone (also known as 1-Methyl-2-pyrrolidinone).

The acronym "DIPHOS", as used herein, unless otherwise indicated, refers to 1,2-Bis(diphenylphosphino)ethane The term "BINAP" (abbreviation for 2,2'-Bis(diphenylphosphino)-1,1'-binaphthyl), as used herein, unless otherwise indicated, is represented by the following formula:

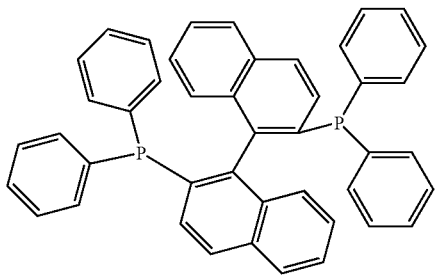

The compounds referred to in the processes of the present invention also include isotopically-labelled compounds, which are identical to compounds referred to herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds referred to in the present invention, prodrugs thereof, and pharmaceutically acceptable salts of said compounds or of said prodrugs which contain the aforementioned isotopes and/or other isotopes of other atoms are within the scope of such compounds. Certain isotopically-labelled compounds referred to in the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

Each of the patents, patent applications, published International applications, and scientific publications referred to in this patent application is incorporated herein by reference in its entirety.

DETAILED DESCRIPTION OF THE INVENTION

General synthetic methods which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) and WO 01/40217 (published Jul. 7, 2001) (Pfizer, Inc.).

Compounds of the formula I may also be prepared according to the following reaction scheme and discussion. Unless otherwise indicated, $R^1$, $R^2$, $R^3$ and $R^4$ in the reaction scheme and discussion that follow are as defined above.

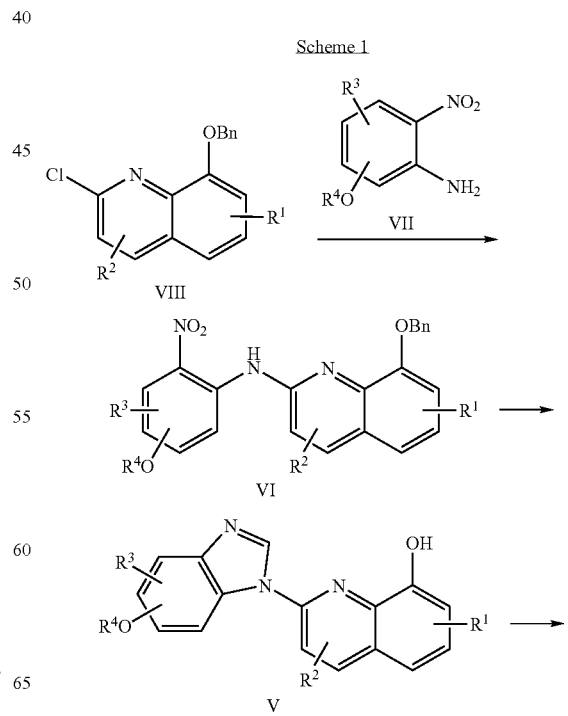

-continued

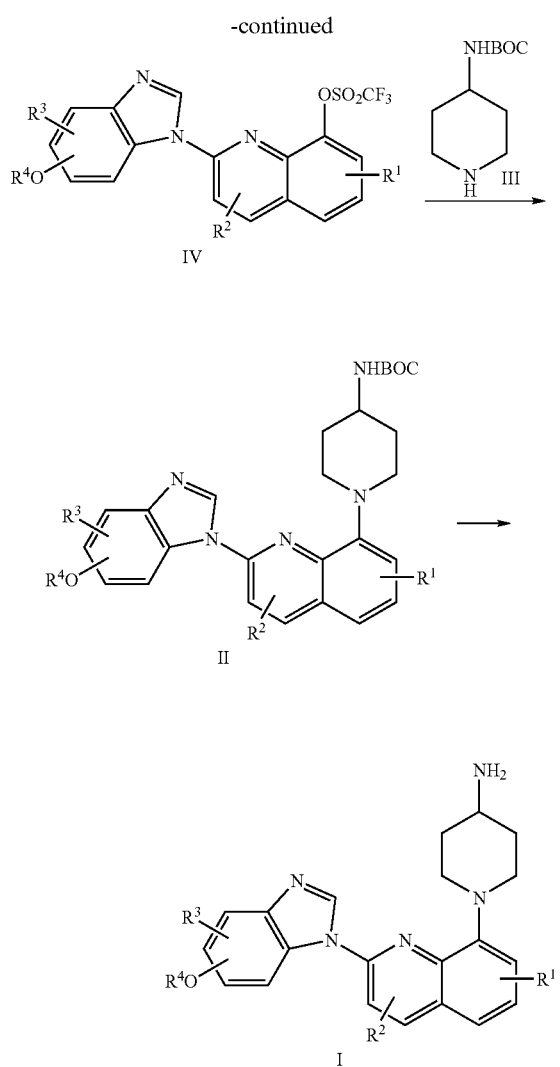

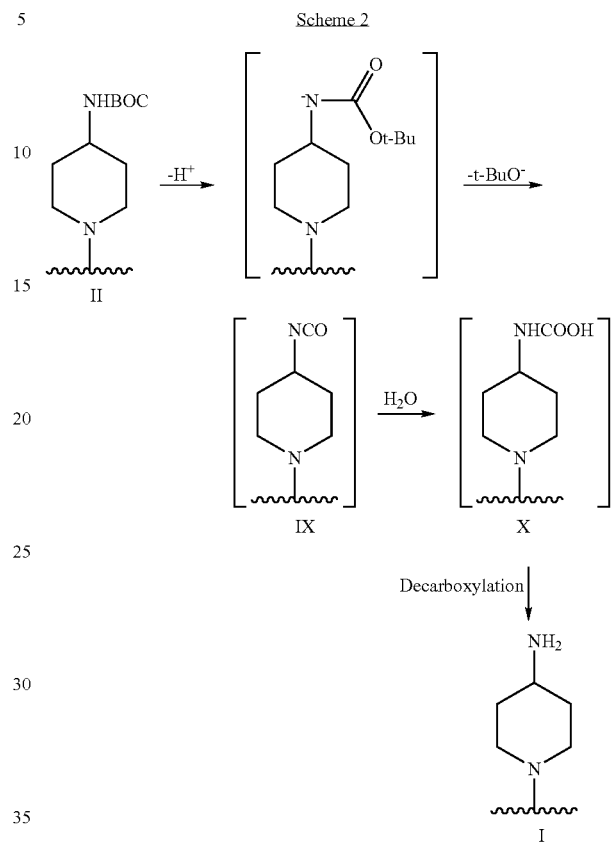

With reference to Scheme I above, the compond of formula I may be prepared starting with the palladium amination of reaction of a 2-chloro-8-benzyloxyquinoline (VIII) and an appropriate 2-amino-nitrobenzene (VII) to provide the quinoline (VI). Reduction of the nitro group and removal of the benzyl group via catalytic hydrogenation, followed by addition of formamidine acetate provides the benzimidazole (V) which can then be transformed into the corresponding triflate (IV). A second palladium catalyzed amination with amine (III) provides piperidinyl quinoline (II) and subsequent removal of the t-butyloxycarbonyl group provides (I).

While not wishing to be bound by theory, the presently claimed process for the preparation of the compounds of formula I from the compounds of formula II under basic (alkaline) conditions is believed to proceed through an isocyanate intermediate (IX) that results from the deprotonation (of the NH proton) of (II) followed by elimination of the t-butoxy group. Hydrolysis of the isocyanate (IX) is believed to produce a carbamic acid (X), which undergoes decarboxylation to produce (I). This mechanism is illustrated in Scheme 2 below. The presence of water as a reactant can be explained by this mechanism.

The reaction of the compound of formula VII with the compound of formula VII in the presence of palladium acetate and DIPHOS (1,2-Bis(diphenylphosphino)ethane) to produce the compound of formula VI is particularly and unexpectedly advantageous compared to the same reaction using palladium acetate, BINAP and PhB(OH)$_2$. The reaction in the presence of DIPHOS results in higher (e.g., 15–25% higher) yields of the product and takes less time to go to completion, particularly in high scale (e.g., 100 grams and higher) synthesis. This process has significant commercial advantages for the production of active ingredients for use in the preparation of a drug.

The starting materials employed in Scheme 1 are readily commercially available or readily prepared useing methods well known to those of ordinary skill in the art.

In each of the reactions discussed or illustrated in the Schemes, pressure is not critical unless otherwise indicated. Pressures from about 0.5 atmospheres to about 5 atmospheres are generally acceptable, and ambient pressure, i.e., about 1 atmosphere, is preferred as a matter of convenience.

The examples and preparations provided below further illustrate and exemplify the compounds of the present invention, methods of preparing such compounds, and the methods of the present invention. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Where HPLC chromatography is referred to in the preparations and examples below, the general conditions used, unless otherwise indicated, are as follows. The column used is a ZORBAX RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/minute.

The present invention is illustrated by the following Examples. It will be understood, however, that the invention is not limited by the specific details of the following Examples.

EXAMPLE 1

Preparation of 4-(3-Methyl-oxetan-3-ylmethoxy)-2-nitro-phenylamine

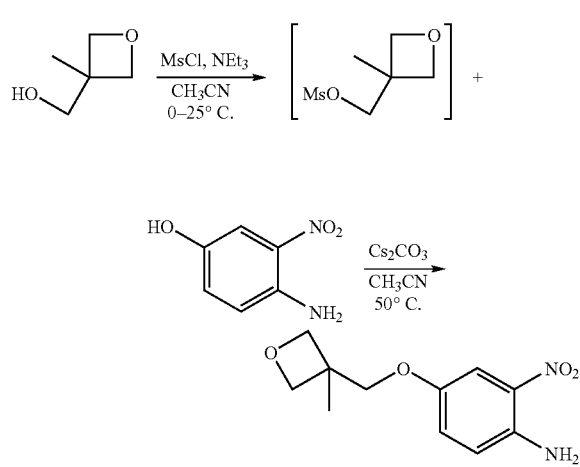

The compound, 3-methyl-3-oxetanemethanol (4.68 g, 45.8 mmol, 1.05 equivalent), acetonitrile (25 mL, 5 volumes), and triethylamine (6.7 mL, 48 mmol, 1.1 equivalent) were charged to a 100 mL round bottomed flask and then cooled to 5–15° C. Methanesulfonyl chloride (3.4 mL, 43.6 mmol, 1.0 equivalent) was charged at a rate which kept the temperature below 45° C. The mixture was stirred at 15–20° C. for 2–6 hours, then cooled to 0–5° C. The solids were filtered through a pad of Celite, then the flask and the filter cake were washed once with 10 mL of acetonitrile. Thereafter, 4-amino-3-nitrophenol (6.73 g, 43.6 mmol, 1 equivalent) and cesium carbonate (18.5 g, 56.7 mmol, 1.3 equivalents) were charged to the filtrate and the mixture was heated at 45–60° C. for 24 h. Upon reaction completion, ethyl acetate 30 mL, 6 volumes) was charged to the flask. The mixture was stirred for 15–60 min at 35–40° C., and then filtered at 35–40° C. through a pad of Celite. The flask and the filter cake were rinsed with 2 by 6 volumes of ethyl acetate. The filtrate was then washed with 25 volumes of 0.5 N sodium hydroxide solution, followed by 25 volumes of saturated sodium chloride solution. The resulting solution was concentrated to low volume and isopropanol (25 mL, 5 volumes) was added. The solids were granulated at 20–25° C. for at least 10 hours and then collected and dried under vacuum at 40° C. with a slight nitrogen bleed to provide 7.7 g of a reddish orange fluffy solid (74% yield). $^1$H NMR ($d_6$-DMSO): δ 7.41 (d, 1H, J=2.9 Hz), 7.29 (br s, 2H), 7.18 (dd, 1H, J=9.1, 2.9 Hz), 6.98 (d, 1H, J=9.1 Hz), 4.46 (d, 2H, J=5.8 Hz), 4.26 (d, 2H, J=5.8 Hz), 3.98 (s, 2H), 1.32 (s, 3H).

EXAMPLE 2

Preparation of (8-Benzyloxy-quinolin-2-yl)-[4-(3-methyl-oxetan-3-ylmethoxy)-2-nitro-phenyl]-amine

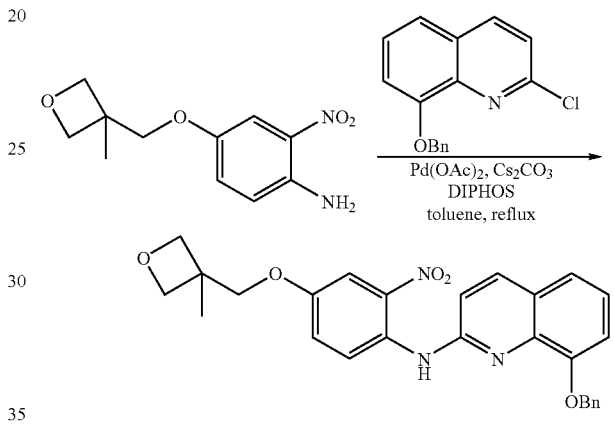

The compound, 8-Benzyloxy-quinolin-2-ol (5 g, 18.5 m,mol, 1.0 equivalent), 4-(3-Methyl-oxetan-3-ylmethoxy)-2-nitro-phenylamine (5.3 g, 22.2 mmol, 1.2 equivalents), cesium carbonate (8.46 g, 26 mmol, 1.4 equivalents), DIPHOS (1,2-Bis(diphenylphosphino)ethane; 443 mg, 111 μmol, 0.06 equivalents) and toluene (75 mL, 15 volumes) were charged to a 100 mL round bottom flask. The reaction was deoxygenated. Palladium acetate (83 mg, 37 μmol, 0.02 equivalents) was added and the reaction was deoxygenated again. The reaction was heated to 100° C. for 24–30 hours. At reaction completion, the reaction was cooled to 55° C. and dichloroethane ("DCE"; 75 mL, 15 volumes) was charged. The slurry was filtered through a pad of Celite and then the flask and filter were rinsed once with additional DCE.(50 mL, 10 volumes). The organics were concentrated to low volume and ethyl acetate (50 mL, 10 volumes) was added. The reaction was heated to reflux and allowed to cool to 20–25° C. The solids were granulated for 10–20 hours, filtered, and dried under vacuum at 40° C. with a slight nitrogen bleed to yield 6.72 g (8-Benzyloxy-quinolin-2-yl)-[4-(3-methyl-oxetan-3-ylmethoxy)-2-nitro-phenyl]-amine as an orange solid (77% yield). The material was judged to be about 95% pure by NMR, with ~5% of the DIPHOS bis-oxide.

$^1$H NMR ($d_6$-DMSO): δ 9.78 (s, 1H), 8.73 (d, 1H, J=9.1 Hz), 8.11 (d, 1H, J=8.7 Hz), 7.55 (m, 2H), 7.36 (m, 4H), 7.22 (m, 4H), 5.20 (s, 2H), 4.52 (d, 2H, J=5.8 Hz), 4.34 (d, 2H, J=5.8 Hz), 4.12 (s, 2H), 1.40 (s, 3H).

EXAMPLE 3

Preparation of 2-[5-(3-Methyl-oxetan-3-ylmethoxy)-benzoimidazol-1-yl]-quinolin-8ol

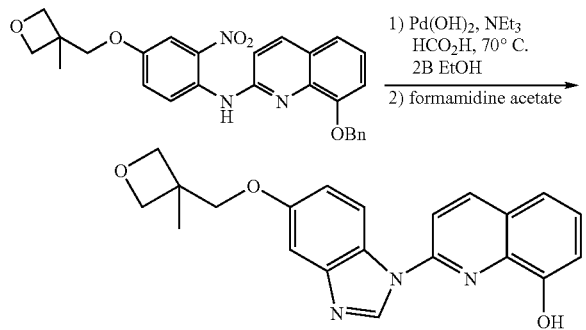

The compound (8-Benzyloxy-quinolin-2-yl)-[4-(3-methyl-oxetan-3-ylmethoxy)-2-nitro-phenyl]-amine (5 g, 10.6 mmol, 1.0 equivalent), ethanol (50 mL, 10 volumes)i triethylamine (7.8 mL, 56.2 mmol, 5.3 equivalents), and palladium hydroxide on carbon (500 mg, 0.1 weight equivalents) were charged to a 100 mL round bottom flask. The solution was deoxygenated and then heated to 50° C. Once the reaction reached 50° C., formic acid (2.2 mL, 56.2 mmol, 5.3 equivalents) was charged slowly to control any exotherm or off-gasing. The reaction was then heated at 55° C. for 15–25 hours. After nitro group reduction and benzyl group removal was noted by APCI MS, the reaction was cooled to 40° C. and filtered through a pad of Celite. The flask and the filter cake were washed once with ethanol (2.5 volumes). The filtrate was then charged to another 100 mL round bottom flask containing formamidine acetate (2.3 g, 22.3 mmol, 2.1 equivalents) and the reaction was heated at reflux for ~8 hours. At reaction completion, the reaction was cooled to 20–25° C. and allowed to granulate for 10–20 hours. The solids were isolated by filtration and dried under vacuum at 40° C. with a slight nitrogen bleed to afford 3.14 g of 2-[5-(3-Methyl-oxetan-3-ylmethoxy)-benzoimidazol-1-yl]-quinolin-8-ol as a yellow solid (82% yield). $^1$H NMR (d$_6$-DMSO): δ 9.88 (s, 1H), 9.25 (s, 1H), 8.61 (d, 1H, J=9.1 Hz), 8.51 (d, 1H, J=9.1 Hz), 8.10 (d, 1H, J=9.1 Hz), 7.44 (m, 2H), 7.35 (d, 1H, J=2.5 Hz), 7.18 (dd, 1H, J=7.5, 1.7 Hz), 7.08 (dd, 1H, J=8.7, 2.5 Hz), 4.51 (d, 2H, J=5.8 Hz), 4.31 (d, 2H, J=5.8 Hz), 4.12 (s, 2H), 1.39 (s, 3H).

EXAMPLE 4

Preparation of Trifluoro-methanesulfonic acid 2-[5-(3-methyl-oxetan-3-ylmethoxy)-benzoimidazol-1-yl]-quinolin-8-yl ester

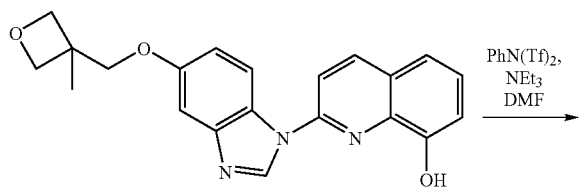

-continued

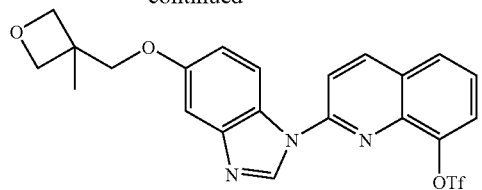

N-Phenyltrifluoromethanesulfonimide (PhN(Tf)$_2$, 2.72 g, 7.6 mmol, 1.1 equivalents), 2-[5-(3-Methyl-oxetan-3-ylmethoxy)-benzoimidazol-1-yl]-quinolin-8-ol(2.5 g, 6.9 mmol, 1.0 equivalent), DMF (7.5 mL, 3 volumes), and then triethylamine (1.9 mL, 13.8 mmol, 2.0 equivalents) were charged to a 50 mL round bottom flask. The slurry was stirred at 20–30° C. for 20–30 hours. After the stirring period, the reaction was filtered and washed with DMF (2.5 mL, 1 volume), followed by isopropyl ether (5 mL, 2 volumes) to yield, after drying under vacuum at 40° C. with a slight nitrogen bleed, 2.9 g trifluoro-methanesulfonic acid 2-[5-(3-methyl-oxetan-3-ylmethoxy)-benzoimidazol-1-yl]-quinolin-8-yl ester as an off-white solid (85% yield).

$^1$H NMR (d$_6$-DMSO): δ 9.18 (s, 1H), 8.75 (d, 1H, J=9.1 Hz), 8.65 (d, 1H, J=8.7 Hz), 8.33 (d, 1H, J=9.1 Hz), 8.18 (dd, 1H, J=8.3, 1.2 Hz), 7.94 (d, 1H, J=8.9 Hz), 7.70 (t, 1H, J=7.9 Hz), 7.36 (d, 1H, J=2.1 Hz), 7.02 (dd, 1H, J=9.1, 2.5 Hz), 4.51 (d, 2H, J=5.8 Hz), 4.31 (d, 2H, J=5.8 Hz), 4.12 (s, 2H), 1.39 (s, 3H).

EXAMPLE 5

Preparation of (1-{2-[5-(3-Methyl-oxetan-3-ylmethoxy)-benzoimidazol-1-yl]-quinolin-8-yl}-piperidin-4-yl)-carbamic acid tert-butyl ester

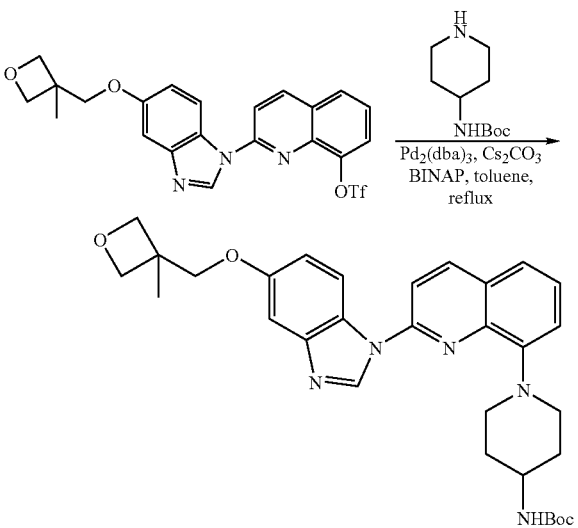

BINAP (379 mg, 608 μmol, 0.06 equivalents), tris(dibenzylideneacetone)dipalladium (186 mg, 203 μmol, 0.02 equivalents) and toluene (35 mL, 7 volumes) were added to a 100 mL round bottom flask. The solution was deoxygenated and stirred at 20–25° C. for ~30 minutes. Next, trifluoro-methanesulfonic acid 2-[5-(3-methyl-oxetan-3-ylmethoxy)-benzoimidazol-1-yl]-quinolin-8-yl ester (5 g, 10.1 mmol, 1 equivalent), piperidin-4-yl-carbamic acid tert-butyl ester (4.06 g, 20.3 mmol, 2.0 equivalents), and cesium carbonate (4.62 g, 14.2 mmol, 1.3 equivalents) were charged. The reaction was again deoxygenated and then heated to 85° C. for 24–32 hours. At reaction completion, the reaction was cooled to 30° C. and dichloroethane (5 volumes) and Celite (0.5 wt. equivalent) were added. The slurry was filtered through a pad of Celite and rinsed with dichloroethane (5 volumes). The mother liquor was then concentrated to low volume and ethyl acetate (75 mL, 15 volumes) was charged. The thin slurry was granulated at 20–25° C. for 8–15 h and then filtered. The mother liquor was collected and washed with a 2.5% $NaH_2PO_4$ solution (3×9 volumes). The organics were again concentrated to low volume and acetonitrile (25 mL, 5 volumes) was charged. The slurry was granulated for 10–20 hours, and then the solids were filtered and dried under vacuum at 40° C. with a slight nitrogen bleed to yield 4.33 g (1-{$^2$-[5-(3-Methyl-oxetan-3-yl-methoxy)-benzoimidazol-1-yl]-quinolin-8-yl}-piperidin-4-yl)-carbamic acid tert-butyl ester as a yellow solid. (79% yield).

$^1$H NMR ($d_6$-DMSO): δ 9.17 (s, 1H), 8.89 (d, 1H, J=8.7 Hz), 8.51 (d, 1H, J=9.1 Hz), 8.15 (d, 1H, J=9.1 Hz), 7.59 (d, 1H, J=8.3 Hz), 7.47 (t, 1H, J=7.9 Hz), 7.35 (m, 2H), 7.29 (m, 1H), 7.14 (d, 1H, J=8.3 Hz), 4.54 (d, 2H, J=5.4 Hz), 4.32 (d, 2H, J=5.8 Hz), 4.13 (s, 2H), 3.75 (d, 2H, J=11.6 Hz), 3.45 (m, 1H), 2.75 (m, 2H), 1.84 (m, 4H), 1.40 (s, 3H), 1.39 (s, 9H).

EXAMPLE 6

Preparation of 1-{2-[5-(3-Methyl-oxetan-3-yl-methoxy)-benzoimidazol-1-yl]-quinolin-8-yl}-piperidin-4-ylamine

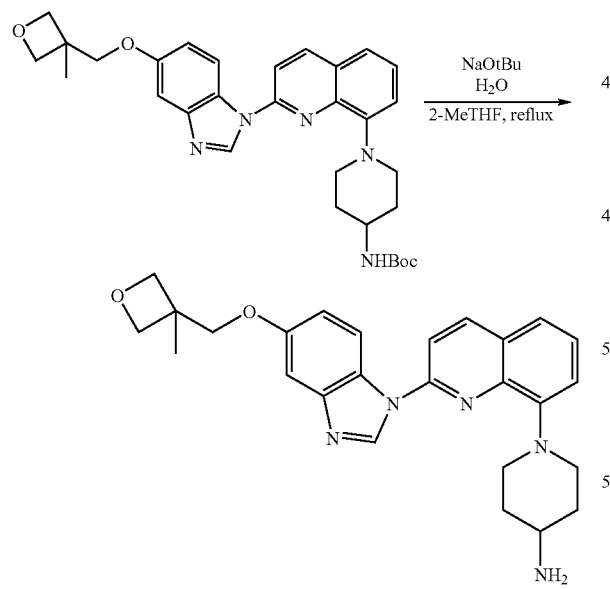

The compound, (1-{2-[5-(3-Methyl-oxetan-3-yl-methoxy)-benzoimidazol-1-yl]-quinolin-8-yl}-piperidin-4-yl)-carbamic acid tert-butyl ester (2 g, 3.68 mmol, 1 equivalent), sodium t-butoxide (1.77 g, 18.4 mmol, 5 equivalents), 2-methyltetrahydrofuran (30 mL, 15 volumes), and water (66 mL, 1 equivalent) were added to a 100 mL round bottom flask. The mixture was heated to reflux and held at reflux for 24–30 hours. At reaction completion, the mixture was cooled to 20–30° C. The reaction was quenched into a 20% citric acid solution (10 volumes) and stirred at 20–30° C. for 30–60 minutes. The citrate salt precipitated out of solution during this time. A 50% sodium hydroxide solution (~1 weight equivalent) was charged to basify the reaction mixture (pH 10–12). The layers were separated at 30–40° C. The aqueous layer was washed with ethyl acetate (10 volumes) and then the combined organics were concentrated to low volume. Ethyl acetate (14 mL, 7 volumes) was charged and the slurry was allowed to granulate for 10–20 hours. The solids were filtered and 1-{2-[5-(3-Methyl-oxetan-3-yl-methoxy)-benzoimidazol-1-yl]-quinolin-8-yl}-piperidin-4-ylamine (1.4 g, 86% yield) was isolated.

$^1$H NMR ($d_6$-DMSO): δ 9.17 (s, 1H), 8.88 (d, 1H, J=8.7 Hz), 8.51 (d, 1H, J=1.9 Hz), 8.14 (d, 1H, J=9.1 Hz), 7.57 (d, 1H, J=7.5 Hz), 7.46 (t, 1H, J=7.9 Hz), 7.37 (d, 1H, J=2.5 Hz), 7.26 (d, 1H, J=7.9 Hz), 7.15 (dd, 1H, J=9.1, 2.5 Hz), 4.53 (d, 2H, J=5.8 Hz), 4.31 (d, 2H, J=5.8 Hz), 4.13 (s, 2H), 3.71 (d, 2H, J=10.4 Hz), 2.73 (m, 3H), 1.87 (d, 2H, J=11.4 Hz), 1.77 (m, 2H), 1.39 (s, 3H).

EXAMPLE 7

Preparation of 1-{2-[5-(3-Methyl-oxetan-3-yl-methoxy)-benzoimidazol-1-yl]-quinolin-8-yl}-piperidin-4-ylamine benzenesulfonate

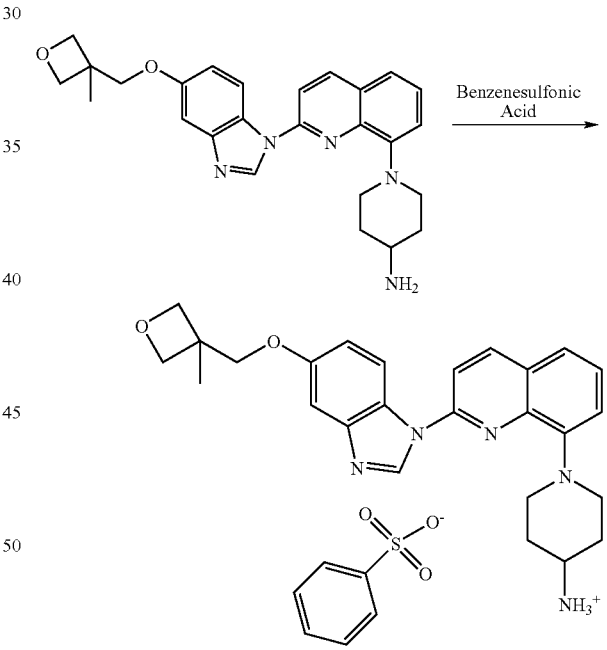

The compound, 1-{2-[5-(3-Methyl-oxetan-3-ylmethoxy)-benzoimidazol-1-yl]-quinolin-8-yl}-piperidin-4-ylamine (2.44 9, 5.5 mmol, 1 equivalent) and ethanol (24 mL, 10 volumes) were added to a 100 mL round bottom flask. The solution was heated to reflux to dissolve the starting material and then cooled to room temperature. A solution of benzenesulfonic acid (918 mg, 5.2 mmol, 0.95 equivalents) in ethanol (5 mL, 2 volumes) was charged and the reaction was heated to reflux for ~30 minutes. The reaction was cooled to 20–30° C. and allowed to granulate for 16–32 hours. The material was then filtered and dried under vacuum with a slight nitrogen bleed to afford 1-{2-[5-(3-Methyl-oxetan-3- ylmethoxy)-benzoimidazol-1-yl]-quinolin-8-yl}-piperidin-4-ylamine benzenesulfonate (2.8 g, 85% yield) as an off-white solid.

$^1$H NMR (d$_6$-DMSO): δ 9.19 (s, 1H), 8.87 (d, 1H, J=9.1 Hz), 8.54 (d, 1H, J=9.1 Hz), 8.16 (d, 1H, J=9.1 Hz), 7.94 (br s, 3H), 7.63 (d, 1H, J=7.5 Hz), 7.56 (m, 2H), 7.48 (t, 1H, J=7.9 Hz), 7.39 (d, 1H, J=2.5 Hz), 7.26 (m, 5H), 4.53 (d, 2H, J=5.8 Hz), 4.31 (d, 2H, J=5.8 Hz), 4.12 (s, 2H), 3.83 (m, 2H), 3.2 (m, 1H), 2.78 (m, 2H), 2.05 (m, 2H), 1.95 (m, 2H), 1.39 (s, 3H).

The invention claimed is:

1. A process for preparing a compound of the formula I

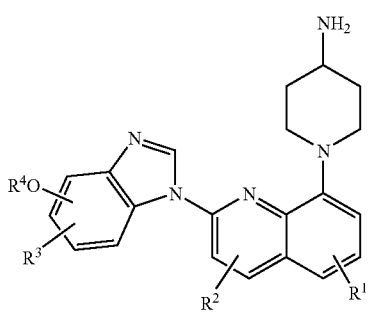

or a pharmaceutically acceptable salt, prodrug, hydrate or solvate thereof; wherein each R$^1$, R$^2$, and R$^3$ is independently selected from the group consisting of H, (C$_1$–C$_6$) alkyl, (C$_3$–C$_6$)cycloalkyl, halo, cyano, CF$_3$, difluoromethoxy, trifluoromethoxy, —O(C$_1$–C$_6$)alkyl, —O(C$_3$–C$_6$)cycloalkyl, and —NR$^{12}$R$^{13}$;

wherein R$^4$ is —(CR$^5$R$^6$)$_m$H, or —(CR$^7$R$^8$)$_n$(4 to 10 membered)-aromatic or nonaromatic heterocyclic containing one or more heteroatoms each selected from O, S and N, wherein m is an integer ranging from 1 to 5, wherein n is an integer ranging from 0 to 5, wherein said 4 to 10 membered heterocyclic when aromatic is optionally substituted by 1 to 3 R$^9$ substituents, and wherein said 4 to 10 membered heterocyclic when non-aromatic is optionally substituted by 1 to 3 R$^{10}$ substituents at any position and optionally substituted by 1 to 3 R$^{11}$ substituents at any position not adjacent to or directly attached to a heteroatom;

wherein each R$^5$, R$^6$, R$^7$ and R$^8$ are independently selected from the group consisting of H and (C$_1$–C$_6$) alkyl;

wherein each R$^9$ is independently selected from H, (C$_1$–C$_6$)alkyl, (C$_3$–C$_6$)cycloalkyl, halo, cyano, CF$_3$, difluoromethoxy, trifluoromethoxy, —O(C$_1$–C$_6$)alkyl, —O(C$_3$–C$_6$)cycloalkyl, and —NR$^{14}$R$^{15}$;

wherein each R$^{10}$ is independently selected from H, (C$_1$–C$_6$)alkyl, and (C$_3$–C$_6$)cycloalkyl;

wherein each R$^{11}$ is independently selected from halo, cyano, CF$_3$, difluoromethoxy, trifluoromethoxy, —O(C$_1$–C$_6$)alkyl, —O(C$_3$–C$_6$)cycloalkyl, and —NR$^{16}$R$^{17}$;

wherein R$^{12}$, R$^{13}$, R$^{14}$, R$^{15}$, R$^{16}$ and R$^{17}$ are independently selected from the group consisting of H, (C$_1$–C$_6$)alkyl, and (C$_3$–C$_6$)cycloalkyl;

wherein each of the aforesaid (C$_1$–C$_6$)alkyl, (C$_3$–C$_6$) cycloalkyl, —O(C$_1$–C$_6$)alkyl and —O(C$_3$–C$_6$)cycloalkyl substituents wherever they occur may optionally be independently substituted by one to three substituents independently selected from the group consisting of halo, cyano, amino, (C$_1$–C$_6$)alkylamino, [(C$_1$–C$_6$)alkyl]$_2$-amino, perhalo(C$_{-C6}$)alkyl, perhalo (C$_1$–C$_6$)alkoxy, (C$_1$–C$_6$)alkyl, (C$_2$–C$_6$)alkenyl, (C$_2$–C$_6$)alkynyl, hydroxy, and (C$_1$–C$_6$)alkoxy; comprising reacting a compound of the formula II

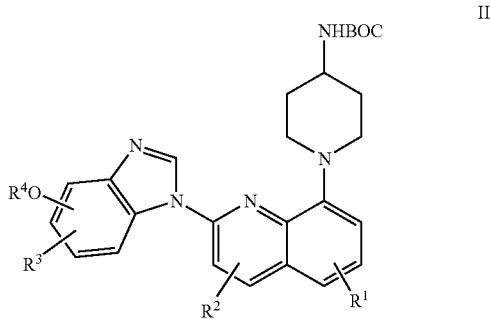

wherein BOC is t-butoxycarbonyl, and R$^1$, R$^2$, R$^3$ and R$^4$ are as defined above for the compound of formula I, with a metal alkoxide in the presence of water to give a compound of the formula I.

2. A process according to claim 1, wherein each R$^1$, R$^2$, and R$^3$ is independently selected from the group consisting of H, (C$_1$–C$_6$)alkyl, and (C$_3$–C$_6$)cycloalkyl, halo, and cyano.

3. A process according to claim 1, wherein R$^4$ is —(CR$^5$R$^6$)$_n$H.

4. A process according to claim 1, wherein R$^4$ is —(CR$^7$R$^8$)$_n$(4 to 10 membered)-aromatic heterocyclic, wherein n is an integer from 0 to 5 and wherein said 4 to 10 membered aromatic heterocyclic is optionally substituted by 1 to 3 R$^9$ substituents.

5. A process according to claim 4, wherein R$^4$ is —(CH$_2$)$_n$ (4 to 10 membered)-aromatic heterocyclic), wherein n is 1 to 4 and wherein said 4 to 10 membered aromatic heterocyclic is optionally substituted by 1 R$^9$ substituent.

6. A process according to claim 5, wherein R$^4$ is —(CH$_2$)$_n$(4 to 6 membered)-aromatic heterocyclic), wherein n is 1 and wherein said 4 to 6 membered aromatic heterocyclic is optionally substituted by 1 R$^9$ substituent.

7. A process according to claim 4, wherein said 4 to 10 membered aromatic heterocyclic is selected from the group consisting of pyridinyl, pyrimidinyl, pyrazinyl, quinolinyl, isoquinolinyl, pyrrolyl, pyrazolyl, imidazolyl, thiophenyl, furanyl, indolyl and benzofuranyl.

8. A process according to claim 4, wherein R$^9$ is selected from the group consisting of H, (C$_1$–C$_6$)alkyl, (C$_3$–C$_6$) cycloalkyl, halo, and cyano.

9. A process according to claim 8, wherein (C$_1$–C$_6$)alkyl is selected from the group consisting of methyl, ethyl, propyl, butyl, and pentyl.

10. A process according to claim 9, wherein (C$_1$–C$_6$)alkyl is methyl.

11. A process according to claim 4, wherein each R$^7$ and R$^8$ is independently selected from methyl, ethyl, propyl and butyl.

12. A process according to claim 4, wherein said 4 to 10 membered aromatic heterocyclic contains one to four heteroatoms each selected from O, S and N, with the proviso that said 4 to 10 membered aromatic heterocyclic does not contain two adjacent O or S atoms.

13. A process according to claim 12, wherein said 4 to 10 membered aromatic heterocyclic contains one to four O atoms with the proviso that said 4 to 10 membered aromatic heterocyclic does not contain two adjacent O atoms.

14. A process according to claim 13, wherein said 4 to 10 membered aromatic heterocyclic contains one to two O atoms.

15. A process according to claim 14, wherein said 4 to 10 membered aromatic heterocyclic contains one O atom.

16. A process according to claim 12, wherein said 4 to 10 membered aromatic heterocyclic contains one to four N atoms.

17. A process according to claim 16, wherein said 4 to 10 membered aromatic heterocyclic contains one to two N atoms.

18. A process according to claim 17, wherein said 4 to 10 membered aromatic heterocyclic contains one N atom.

19. A process according to claim 1, wherein $R^4$ is —$(CR^7R^8)_n$(4 to 10 membered)-non-aromatic heterocyclic, wherein n is an integer from 0 to 1 and wherein said 4 to 10 membered nonaromatic heterocyclic group is optionally substituted by 1 to 3 $R^{10}$ substituents.

20. A process according to claim 19, wherein $R^4$ is —$(CR^7R^8)_n$(4 to 8 membered)-non-aromatic heterocyclic, wherein n is an integer from 0 to 1 and wherein said 4 to 8 membered non-aromatic heterocyclic is optionally substituted by 1 to 3 $R^{10}$ substituents.

21. A process according to claim 20, wherein $R^4$ is —$(CR^7R^8)_n$(4 to 6 membered)-non-aromatic heterocyclic, wherein n is an integer from 0 to 1 and wherein said 4 to 6 membered non-aromatic heterocyclic is optionally substituted by 1 to 3 $R^{10}$ substituents.

22. A process according to claim 21, wherein $R^4$ is —$(CR^7R^8)_n$(6 membered)-non-aromatic heterocyclic, wherein n is an integer from 0 to 1 and wherein said 6 membered non-aromatic heterocyclic is optionally substituted by 1 to 3 $R^{10}$ substituents.

23. A process according to claim 22, wherein $R^4$ is —$(CR^7R^8)_n$(5 membered)-non-aromatic heterocyclic, wherein n is an integer from 0 to 1 and wherein said 5 membered non-aromatic heterocyclic is optionally substituted by 1 to 3 $R^{10}$ substituents.

24. A process according to claim 23, wherein $R^4$ is —$(CR^7R^8)_n$(4 membered)-non-aromatic heterocyclic, wherein n is an integer from 0 to 1 and wherein said 4 membered non-aromatic heterocyclic is optionally substituted by 1 to 3 $R^{10}$ substituents.

25. A process according to claim 19, wherein said 4 to 10 membered non-aromatic heterocyclic is selected from the group consisting of tetrahydrothiopyranyl, thiomorpholino, dioxanyl, pyrrolidinyl, tetrahydrofuranyl, tetrahydropyranyl, piperidino, morpholino, piperazinyl, homopiperazinyl, azetidinyl, oxetanyl, homopiperidinyl, 3-azabicyclo[3.1.0] hexanyl, 3-azabicyclo[4.1.0]heptanyl, azabicyclo[2.2.2] hexanyl, 3H-indolyl, and 4H-pyranyl.

26. A process according to claim 25, wherein said 4 to 10 membered non-aromatic heterocyclic is selected from the group consisting of tetrahydrothiopyranyl, thiomorpholino, dioxanyl, tetrahydrofuranyl, tetrahydropyranyl, piperidino, morpholino, piperizinyl and oxetanyl.

27. A process according to claim 26, wherein said 4 to 10 membered heterocyclic is selected from the group consisting of tetrahydrofuranyl, morpholino and oxetanyl.

28. A process according to claim 1, wherein the compound of formula I is selected from the group consisting of:
1-{2-[5-(3-Morpholin-4-yl-propoxy)-benzoimidazol-1-yl]-quinolin-8-yl}-piperidin-4-ylamine;
(±)-1-{2-[5-(Tetrahydro-furan-3-yloxy)-benzoimidazol-1-yl]-quinolin-8-yl}-piperidin-4-ylamine;
1-{2-[5-(3-Methyl-oxetan-3-ylmethoxy)-benzoimidazol-1-yl]-quinolin-8-yl}-piperidin-4-ylamine;
1-{2-[5-(Tetrahydro-pyran-4-yloxy)-benzoimidazol-1-yl]-quinolin-8-yl}-piperidin-4-ylamine; and the pharmaceutically acceptable salts, prodrugs, hydrates and solvates of the foregoing compounds.

29. A process according to claim 28, wherein the salt is the benzenesulfonate salt.

30. A process according to claim 29, wherein the compound of formula I is the benzenesulfonate salt of 1-{2-[5-(3-Methyl-oxetan-3-ylmethoxy)-benzoimidazol-1-yl]-quinolin-8-yl}-piperidin-4-ylamine.

31. A process according to claim 1, wherein the water is present in an amount of about 1 equivalent.

32. A process according to claim 1, wherein the reaction is performed in the presence of an ether solvent.

33. A process according to claim 32, wherein the ether is a cyclic ether.

34. A process according to claim 33, wherein the cyclic ether is tetrahydrofuran, 2-methyl tetrahydrofuran, or a mixture thereof.

35. A process according to claim 34, wherein the cyclic ether is 2-methyl tetrahydrofuran.

36. A process according to claim 1, wherein the reaction is performed at a temperature of about 60° C. to about 80° C.

37. A process according to claim 1, wherein the metal is an alkaline earth metal.

38. A process according to claim 37, wherein the alkaline earth metal is sodium or potassium.

39. A process according to claim 1, wherein the alkaline earth metal alkoxide is a ($C_1$–$C_6$)alkoxide.

40. A process according to claim 1, wherein the alkaline earth metal alkoxide is sodium t-butoxide.

* * * * *